United States Patent [19]

Leonard et al.

[11] 4,180,681
[45] Dec. 25, 1979

[54] PREPARATION AND RECOVERY OF METHACRYLIC ACID FROM AN AQUEOUS SODIUM METHACRYLATE SOLUTION

[75] Inventors: John J. Leonard, Springfield; Harold Shalit, Bala Cynwyd, both of Pa.

[73] Assignee: Atlantic Richfield Company, Los Angeles, Calif.

[21] Appl. No.: 934,766

[22] Filed: Aug. 17, 1978

[51] Int. Cl.$^2$ .............................................. C07C 57/04
[52] U.S. Cl. ................................. 562/600; 562/598
[58] Field of Search ................ 562/600, 608; 562/598

[56] References Cited

U.S. PATENT DOCUMENTS

| | | | |
|---|---|---|---|
| 3,761,332 | 12/1973 | Sato et al. | 562/600 |
| 3,839,437 | 10/1974 | Wang et al. | 562/533 |
| 3,868,417 | 2/1975 | Duembgen et al. | 562/600 |

OTHER PUBLICATIONS

Kirk–Othmer "Encyclopedia of Chemical Technology" 2nd Ed. (1963) vol, 1, pp. 715–717.

*Primary Examiner*—Bernard Helfin
*Assistant Examiner*—L. Hendriksen
*Attorney, Agent, or Firm*—Delbert E. McCaslin

[57] ABSTRACT

A process for the recovery of methacrylic acid formed from an aqueous sodium methacrylate solution derived from the silver catalyzed oxidation reaction of methacrolein and an aqueous solution of sodium hydroxide which comprises contacting the aqueous sodium methacrylate solution at a suitable temperature, in the presence of a high gaseous carbon dioxide pressure, with a water immiscible alkane, cycloalkane, alkyl benzene, or carboxylic acid ester solvent to extract and form a methacrylic acid-containing organic solvent phase, an aqueous phase and a precipitated sodium bicarbonate solid phase and recovering the methacrylic acid from the organic solvent phase. Liquid $CO_2$ which may be employed with the water immiscible solvent at 800 psig may also be employed alone at its equilibrium vapor pressure as the reactant and extractant medium.

2 Claims, No Drawings

PREPARATION AND RECOVERY OF METHACRYLIC ACID FROM AN AQUEOUS SODIUM METHACRYLATE SOLUTION

BACKGROUND OF THE INVENTION

In U.S. Pat. Nos. 2,887,496 and 2,930,801 there is disclosed processes for the preparation of methacrylic acid by (1) the oxidation of methacrolein in aqueous sodium hydroxide solution in the presence of a silver catalyst to produce the sodium salt of the methacrylic acid, i.e., an aqueous sodium methacrylate solution, which solution is (2) treated with a strong acid such as sulfuric to liberate the methacrylic acid from the sodium salt. The free acid can be separated by appropriate methods such as ether extraction.

The present invention is directed to an effective method of recovering the methacrylic acid from an aqueous sodium methacrylate solution produced, for example, by the above described processes by contacting the aqueous sodium methacrylate solution after separation of the silver catalyst, for example, by filtration, at a suitable temperature with a water immiscible alkane, cycloalkane, alkyl benzene, or carboxylic acid ester solvent to extract the methacrylic acid formed in the presence of a high carbon dioxide pressure to acidify the aqueous solution. Liquid carbon dioxide at its equilibrium vapor pressure may also be employed at temperatures of from about 0° C. to 30° C. to react with the sodium methacrylate and extract the methacrylic acid formed with the precipitation of sodium bicarbonate.

Since the solubility of sodium bicarbonate in water is relatively high, an essential feature of the recovery process of the invention is the use of high $CO_2$ pressures in conjunction with a water immiscible organic solvent to (1) lower the solubility of the precipitated sodium bicarbonate (formed by the reaction) in water and (2) provide and allow for an effective extraction of the methacrylic acid formed respectively thus, shifting the equilibrium reaction to the right to completion and high acid recovery in accordance with the following:

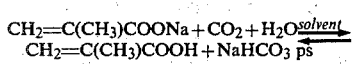

A free methacrylic acid-containing organic solvent phase is formed along with an aqueous phase and a precipitated sodium bicarbonate phase. The phases may be separated by any conventional method, e.g., decantation, filtration and centrifugation. The methacrylic acid may be separated and recovered from the organic solvent phase by for example distillation; the organic solvent being recovered for recycle. Liquid carbon dioxide at its equilibrium vapor pressure at temperatures of from about 0° C. to 30° C. may also be employed in the reaction, without additional solvent, to also act as the water immiscible organic solvent phase for extraction of the methacrylic acid as formed. After separation of the aqueous and precipitated sodium bicarbonate phases, the methacrylic acid may be recovered from the liquid $CO_2$-containing methacrylic acid phase by lowering the pressure to form $CO_2$ gas which may be released leaving the methacrylic acid product. Aqueous sodium methacrylate solutions are not neutralized to any significant extent by carbon dioxide alone due to an unfavorable equilibrium except as high $CO_2$ pressures and in the presence of an organic phase.

U.S. Pat. No. 3,839,437, describes a process of preparing methacrylic acid by employing calcium hydroxide to form the metal salt of the acid, calcium methacrylate, and neutralization with $CO_2$ at low pressure to give the acid and the insoluble calcium carbonate in the presence of a water immiscible organic solvent, such as an ether, to extract the methacrylic acid from the aqueous phase. Continuous passage of carbon dioxide with ether extraction gave only 10.6 and 41.3 percent methacrylic acid recovery in 1 and 4 hours respectively.

British Pat. No. 1,055,229 discloses a process for the use of carbon dioxide to neutralize calcium methacrylate formed by oxidizing methacrolein in an aqueous medium of an alkaline earth metal hydroxide using cupric oxide or hydroxide and a noble metal, noble metal oxide or hydroxide. The methacrylic acid is recovered by acidification with a mineral acid.

French Pat. No. 1,503,918 discloses a process for the silver catalyzed oxidation of methacrolein to prepare an aqueous solution of sodium methacrylate.

U.S. Pat. No. 3,579,572 describes a process in which carbon dioxide is employed to treat an aqueous lithium or magnesium terephthalate under pressure to precipitate terephthalic acid.

Many important commercial applications have been developed for the methacrylic acid product of this invention, significantly, for the preparation of acrylate type polymers and resins.

SUMMARY OF THE INVENTION

In accordance with the present invention there is provided an economically improved process for recovering methacrylic acid from an aqueous sodium methacrylate solution, which solution, is derived from a silver catalyzed oxidation of methacrolein in an aqueous solution of sodium hydroxide to produce the methacrylic acid salt of sodium, for example, by the processes set forth and described in U.S. Pat. Nos. 2,887,496 and 2,930,801 and French Pat. No. 1,503,918 noted hereinabove and incorporated herein by reference.

It is an object of this invention to provide a process for the substantial recovery of methacrylic acid from aqueous solutions containing sodium methacrylate.

It is another object of this invention to provide an economically improved process for the recovery of methacrylic acid from aqueous sodium methacrylate solutions derived from the silver catalyzed oxidation, with oxygen or an oxygen-containing gas, of methacrolein in an aqueous sodium hydroxide base by utilizing a water immiscible alkane, cycloalkane, alkyl benzene, or carboxylic acid ester solvent to extract the methacrylic acid under a high pressure of carbon dioxide.

It is a further object of this invention to provide a process for the recovery of methacrylic acid from aqueous solutions of sodium methacrylate utilizing liquid carbon dioxide, at its equilibrium vapor pressure and at temperatures of from 0° C. to 30° C., solely as reactant and acid extractant.

These and other objects and advantages of this invention will become apparent from the description and from the claims.

DESCRIPTION OF THE INVENTION

According to the present invention, an aqueous sodium methacrylate-containing solution, as for example, an aqueous sodium methacrylate solution obtained by reacting methacrolein and oxygen in the presence of a silver or silver compound catalyst and in an aqueous sodium hydroxide solution, is filtered to remove the silver catalyst and the solution then contacted with a water immiscible alkane, cycloalkanes, alkyl benzenes, or carboxylic acid ester extraction solvent under superatmospheric gaseous carbon dioxide pressure or optionally under liquid $CO_2$ alone to form and precipitate a sodium bicarbonate salt phase and form a methacrylic acid-containing organic phase and an aqueous phase which phases are separated and the organic phase treated to recover the methacrylic acid.

The aqueous sodium methacrylate solutions employed in the process of the present invention and prepared for example, by the processes set forth in U.S. Pat. Nos. 2,887,496 and 2,930,801 and others noted hereinabove, will generally contain about 35 to 50 weight percent sodium methacrylate. Sodium methacrylate is soluble in water up to about 50 weight percent at 25° C. The use of high initial concentrations of sodium methacrylate in aqueous solution in the instant invention is preferred since the "common ion effect" of sodium ion decreases the solubility of the sodium bicarbonate in solution thus, enchancing precipitation of the sodium bicarbonate and recovery of methacrylic acid in the organic solvent phase.

The water immiscible solvents which may be employed may be alkanes having from 5 to 17 carbon atoms such as pentane, heptane, octane, undecane, heptadecane, etc., alkyl benzenes having from 1 to 15 carbon atoms in the alkyl chain such as toluene, xylene, ethyl and propyl benzenes, p-cymene, etc., cycloalkanes such as cyclohexane, decalin, cyclopentane, tetralin, methylcyclohexane, etc., and carboxylic acid esters such as the $C_1$ to $C_4$ phthalate esters, etc. The preferred organic solvents are the alkyl benzenes such as toluene. The solvents may be employed in concentrations of from about 10 to 90 weight percent and preferably from about 30 to 50 weight percent of the total sodium methacrylate-water-solvent feed mixture to be treated to recover the methacrylic acid. Solvents containing naphthalene rings have proven to be inferior as extractant solvents.

The reaction between the sodium methacrylate and carbon dioxide may be carried out in an autoclave or any other pressure reactor. Generally the aqueous sodium methacrylate solution and the water immiscible organic solvent in the desired weight ratio are charged to the autoclave and the carbon dioxide introduced to the desired reaction pressure. Liquid carbon dioxide is charged at 800 psig when used as reactant and extractant. The reaction can be carried out batchwise or as a continuous process and the order of addition of materials may also be varied to suit the particular apparatus employed.

In general, a carbon dioxide pressure of about 400 psig to about 800 psig and preferably from 700 psig to 800 psig is employed. Higher pressures may be employed but are avoided since there is no apparent economic improvement. The critical temperature of $CO_2$ is 31° C. Stoichiometric quantities of carbon dioxide are generally employed. However, an excess of carbon dioxide may be employed, for example, in continuous processes where large excess requirements utilized; a suitable recycle of unreacted carbon dioxide may be employed. The reaction will proceed at temperatures of about 0° C. to 50° C. with gaseous carbon dioxide and at temperatures of from about 0° C. to 30° C. Using liquid $CO_2$ alone at its equilibrium vapor pressure which is 506 psig at 0° C., 830 psig at 20° C. and 1046 psig at 30° C. It is generally preferred to operate the process at temperatures in the range of 20° C. to 30° C. to obtain a convenient rate of reaction and recovery of methacrylic acid. Heating and/or cooling means may be employed interior or exterior of the reaction to maintain the temperature with in the desired range.

The following Examples are provided to illustrate the invention in accordance with the principles of this invention but are not to be construed as limiting the invention in any way except as indicated by the appended claims.

In the Examples which follow the aqueous sodium methacrylate solutions were obtained by taking the effluent from a silver catalyzed conversion of methacrolein with oxygen in an aqueous solution of sodium hydroxide as described in U.S. Pat. No. 2,930,801 and French Pat. No. 1,503,918 noted hereinabove. The solutions were filtered to remove the catalyst and contained varying concentrations of aqueous sodium methacrylate. The aqueous sodium methacrylate solutions and water immiscible solvent in desired quantities were charged into a 500 ml stainless steel stirred autoclave and the autoclave pressured to the desired carbon dioxide pressure. Liquid carbon dioxide was charged to the autoclave under 800 psig pressure. The autoclave was heated or cooled to the desired reaction temperature, stirred for one hour unless otherwise noted and the pressure vented and the sodium bicarbonate precipitate filtered off leaving an aqueous phase and a methacrylic acid-organic phase. The aqueous phase included minor amounts of unreacted sodium methacrylate and by product sodium carbonate. The aqueous and organic phase are separated and the methacrylic acid recovered from the organic phase. When $CO_2$ is used alone the methacrylic acid is recovered as hereinabove described. The methacrylic acid-organic solvent phase was analyzed by electrometric titration to determine percent recovery of methacrylic acid.

EXAMPLES 1 to 20

In Examples 1 to 20 carbon dioxide gas at various pressures and temperatures was employed along with various water immiscible organic phase solvents to extract and recover methacrylic acid. Process conditions and results are summarized in Table 1. Examples 16 and 17 are comparative Examples showing the use of no organic phase and a naphthalene solvent respectively.

TABLE 1

| Ex. No. | Organic Phase Solvent | %[1] NaMAA | Phase[2] Ratio | Temp. °C. | $CO_2$ psig | Mol %[4] NaMAA Converted | Mol %[5] MAA Recovered |
|---|---|---|---|---|---|---|---|
| 1 | toluene | 50 | 1:1 | 20 | 500 | 38 | 35 |
| 2 | p-cymene | 50 | 1:1 | 25 | 500 | 33 | 29 |
| 3 | toluene | 27 | 1:1 | 25 | 400 | 30 | 28 |
| 4 | toluene | 40 | 1:1 | 25 | 750 | 54 | 45 |
| 5 | toluene | 50 | 1:1 | 25 | 750 | 56 | 48 |
| 6[3] | toluene | 50 | 1:1 | 25 | 750 | 55 | 45 |

TABLE 1-continued

| Ex. No. | Organic Phase Solvent | %[1] NaMAA | Phase[2] Ratio | Temp. °C | CO$_2$ psig | Mol %[4] NaMAA Converted | Mol %[5] MAA Recovered |
|---|---|---|---|---|---|---|---|
| 7 | toluene | 50 | 2:1 | 20 | 600 | 68 | 67 |
| 8 | toluene | 35 | 1:1 | 40 | 750 | 61 | 60 |
| 9 | xylene | 50 | 1:1 | 20 | 750 | 69 | 65 |
| 10 | tetralin | 50 | 1:1 | 20 | 750 | 54 | 45 |
| 11 | decalin | 50 | 1:1 | 20 | 750 | 50 | 39 |
| 12 | dibutyl phthalate | 50 | 1:1 | 25 | 750 | 48 | 39 |
| 13 | undecane | 50 | 2:1 | 25 | 750 | 55 | 42 |
| 14 | DIPB[6] | 50 | 1:1 | 20 | 750 | 57 | 44 |
| 15 | toluene | 50 | 1:1 | 25 | 800[7] | 67 | 65 |
| 16 | none[8] | 50 | 1:1 | 25 | 750 | 4 | 0 |
| 17 | dimethylnaphthalene[8] | 40 | 1:1 | 25 | 750 | 18 | 10 |
| 18 | heptane | 50 | 1:1 | 30 | 750 | 57 | 48 |
| 19 | cyclohexane | 50 | 1:1 | 35 | 700 | 51 | 40 |
| 20 | methylcyclohexane | 50 | 2:1 | 25 | 750 | 52 | 43 |

[1] weight % sodium methacrylate (NaMAA) in aqueous solution
[2] volume of organic phase solvent/volume of aqueous NaMAA
[3] time of reaction 15 minutes
[4] total % conversion of initial sodium methacrylate
[5] % methacrylic acid (MAA) extracted into organic phase and recovered
[6] DIPB - diisopropyl benzene
[7] liquid carbon dioxide
[8] comparative examples

EXAMPLES 21 to 24

In Examples 21 to 24 liquid carbon dioxide was employed alone at its equilibrium vapor pressure to neutralize the sodium methacrylate solution and to act as the water immiscible organic phase to extract the methacrylic acid formed. After a one hour reaction time the CO$_2$-methacrylic acid phase was separated from the aqueous and solid sodium bicarbonate phases. The pressue was released forming CO$_2$ gas and the remaining methacrylic acid dissolved in toluene for analysis by electrometric titration to determine percent recovery. The conditions and results are shown in Table 2.

TABLE 2

| Ex. No. | Temp. °C | % NaMAA[1] | Phase Ratio | Mol %[2] NaMAA Converted | Mol %[3] MAA Recovered |
|---|---|---|---|---|---|
| 21 | 20 | 50 | 1:1 | 35 | 28 |
| 22 | 25 | 50 | 2:1 | 36 | 32 |
| 23 | 25 | 46 | 1:1 | 30 | 29 |
| 24 | 20 | 43 | 1:1 | 36 | 32 |

[1] weight % sodium methacrylate (NaMAA) in aqueous solution
[2] total mol % conversion of initial sodium methacrylate
[3] % methacrylic acid (MAA) extracted into liquid CO$_2$ and recovered

We claim:
1. A process for the recovery of methacrylic acid from an aqueous sodium methacrylate solution derived from the silver catalyzed oxidation reaction of methacrolein in an aqueous solution of sodium hydroxide which comprises the steps of:
contacting the aqueous sodium methacrylate solution at a temperature of from about 0° C. to 30° C. with liquid carbon dioxide at its equilibrium vapor pressure to form a methacrylic acid-containing liquid carbon dioxide phase, an aqueous phase and a precipitated sodium bicarbonate phase;
separating the methacrylic acid-containing liquid carbon dioxide phase from the aqueous phase and the precipitated sodium bicarbonate;
lowering the pressure of the liquid carbon dioxide to form gaseous carbon dioxide;
releasing the gaseous carbon dioxide; and
recovering the methacrylic acid.
2. A process according to claim 1 wherein the process is carried out at a temperature of from about 20° C. to 30° C.

* * * * *